(12) United States Patent
Matsumura

(10) Patent No.: US 8,035,373 B2
(45) Date of Patent: Oct. 11, 2011

(54) DEVICE AND METHOD FOR INSPECTING SCRATCHES ON CELL EXTERNAL CASE

(75) Inventor: Osami Matsumura, Yamaguchi (JP)

(73) Assignee: Toyo Kohan Co., Ltd., Tokyo (JP)

( * ) Notice: Subject to any disclaimer, the term of this patent is extended or adjusted under 35 U.S.C. 154(b) by 742 days.

(21) Appl. No.: 11/718,319

(22) PCT Filed: Oct. 25, 2005

(86) PCT No.: PCT/JP2005/019629
§ 371 (c)(1),
(2), (4) Date: Nov. 26, 2007

(87) PCT Pub. No.: WO2006/046578
PCT Pub. Date: May 4, 2006

(65) Prior Publication Data
US 2008/0129287 A1    Jun. 5, 2008

(30) Foreign Application Priority Data
Oct. 28, 2004   (JP) ................. 2004-313824

(51) Int. Cl.
*G01N 27/82* (2006.01)
(52) U.S. Cl. ................. 324/240; 324/235; 324/242
(58) Field of Classification Search .......... 324/235–242, 324/220–232
See application file for complete search history.

(56) References Cited

U.S. PATENT DOCUMENTS

| | | | |
|---|---|---|---|
| 3,366,874 A * | 1/1968 | Kuhne | 324/207.17 |
| 3,535,624 A * | 10/1970 | Wood | 324/226 |
| 3,710,236 A * | 1/1973 | Halsey et al. | 324/235 |
| 4,468,619 A * | 8/1984 | Reeves | 324/220 |
| 4,594,549 A * | 6/1986 | Smith et al. | 324/232 |
| 4,618,823 A * | 10/1986 | Dahlheimer et al. | 324/207.16 |
| 5,028,869 A * | 7/1991 | Dobmann et al. | 324/223 |
| 5,144,234 A * | 9/1992 | Murata | 324/235 |
| 5,235,275 A * | 8/1993 | Ando et al. | 324/238 |
| 5,293,117 A * | 3/1994 | Hwang | 324/220 |
| 5,357,198 A * | 10/1994 | Ando et al. | 324/242 |
| 6,320,375 B1 * | 11/2001 | Cotton et al. | 324/238 |
| 2003/0011363 A1 * | 1/2003 | Wayman et al. | 324/238 |
| 2003/0038629 A1 * | 2/2003 | Yokota et al. | 324/235 |
| 2007/0222438 A1 * | 9/2007 | Reeves | 324/240 |

FOREIGN PATENT DOCUMENTS

JP     05-107240 A     4/1993

(Continued)

*Primary Examiner* — Jay Patidar
(74) *Attorney, Agent, or Firm* — Browdy and Neimark, PLLC

(57) ABSTRACT

It is possible to accurately and stably inspect a scratch in the vicinity of a surface of a cell external case formed by a cylindrical copper plate by using a simple device. The cell external case (1) is rotated around the center axis of the cylindrical shape by a rotation device (2) and a magnetic flux is applied to the rotating cell external case from both ends of a frame (4). When a scratch is present on the cell external case (1), leak magnetic flux is generated which is detected by a magnetic sensor (6) arranged in the vicinity of the cell external case (1) and displayed on a display device (12) via a signal processing device (11). Since the cylindrical cell external case (1) rotates around its center axis, the distance between its surface and the magnetic sensor (6) is not changed and a scratch can be detected stably.

3 Claims, 4 Drawing Sheets

FOREIGN PATENT DOCUMENTS

| | | |
|---|---|---|
| JP | 08-304346 A | 11/1996 |
| JP | 10-111210 A | 4/1998 |
| JP | 11-30608 A | 2/1999 |
| JP | 11-96981 A | 4/1999 |
| JP | 2002-320925 A | 11/2002 |

* cited by examiner

DEVICE AND METHOD FOR INSPECTING SCRATCHES ON CELL EXTERNAL CASE

TECHNICAL FIELD

The present invention relates to an inspecting device and an inspecting method for automatically inspecting a scratch on a surface of a cylindrical cell external case made of a magnetic material such as a thin steel sheet and displaying the position, etc. of the scratch.

BACKGROUND ART

In common dry cells, external cases are composed of thin steel sheets surface-treated with nickel plating, etc. The external cases can be produced by deep-drawing the thin steel sheet materials into cylindrical shapes, ironing being further carried out optionally thereafter. In the production process such as the deep drawing, the thin steel sheers come into contact with press dies and tools, and are subjected to strong forces, to be greatly deformed.

Incidentally the thin steel sheet materials to be subjected to the deep drawing often have defects such as fine pores of blow holes and non-metal inclusion contaminations, which are inevitably generated in the production of the materials. When the thin steel sheet material has such defects, scratches such as cracks are often formed around the defects during the process of deep drawing, etc. The scratches are so fine that it is almost impossible to visually find the scratches, even surface ones. Further, even when the thin steel sheet material has no defects, the material comes into contact with press dies, etc. during the forming process, whereby in some cases scratches are formed in the vicinity of the surface of the cylindrical-shaped material.

In a case where a dry cell is used for a long period, a liquid might leak from the cell due to deterioration of an electrolyte, etc., and thereby an electronics device using the dry cell as a power source is contaminated and deteriorated. Further, in a case where a plurality of dry cells are used in series and one cell is connected in the incorrect opposite polar direction, a reverse current passes through the cell, and thereby a gas can be generated to rupture the cell. The thin steel sheets used for the external cases of the dry cells have small thickness of 0.1 to 0.2 mm, whereby the scratches on the external cases can cause liquid leakage and rupture. Thus, the dry cell external cases having scratches in the vicinity of the surfaces must be rejected as inferior products.

Magnetism search methods have been known as methods for inspecting scratches on steel sheet surfaces. As shown in FIG. 6, a magnetic flux in the vicinity of a steel sheet surface is distorted and leaks from the surface in a position with a defect such as a crack, and the above methods utilize this phenomenon. By detecting the leak magnetic flux with a magnetic sensor, the scratches in the vicinity of the steel sheet surface can be inspected. The leak magnetic flux may be detected by spreading iron powder and by visually observing its aggregation state, instead of using the magnetic sensor.

A device for detecting a leak magnetic flux by using a magnetic sensor, thereby inspecting a scratch on a steel sheet surface, is disclosed in JP-A-56-1645. The device, shown in FIG. 7, is used for inspecting a scratch on an object material of a steel sheet 20. A detection unit 21 is attached to a guide bar 8 and placed above the steel sheet 20. The detection unit 21 has a C-shaped frame 4, which has ends of legs immediately above the steel sheet 20, and an exciting coil 5 is attached to the center of the frame 4. Further, the detection unit 21 has a plurality of magnetic sensors 6 arranged in the vicinity of the steel sheet 20, aid the distance between each magnetic sensor 6 and the steel sheet 20 is 1 mm or less.

To inspect a scratch, the frame 4 is converted to an electromagnet by applying a current to the exciting coil 15. Thus, in the case of using the leg 4A as an N pole, a magnetic flux passes from the leg 4A into the S pole leg 4B, across the surface of the steel sheet 20. In this case, when the steel sheet 20 has a scratch (or a defect), the magnetic flux leaks from the surface of the steel sheet 20, and the leak magnetic flux is detected by the magnetic sensors 6. The detection signal is processed by a signal processing device (not shown), to measure position of a scratch. The detection unit 21 is guided by the guide bar 8 and moved in the width direction of the steel sheet 20, and scans the steel sheet 20 to inspect a scratch.

Patent Document 1: JP-A-56-61645

DISCLOSURE OF THE INVENTION

Problems that the Invention is to Solve

In the methods of detecting leak magnetic flux, thereby inspecting scratches on steel sheets, fine scratches in the vicinity of steel sheet surface can be detected only by a relatively simple device. However, the conventional methods of detecting leak magnetic flux are used only for inspecting scratches on flat materials of steel sheets, etc. as described in Patent Document 1. The object materials of the cell external cases have cylindrical structure, and thus scratches thereon cannot be inspected only by moving a magnetic sensor parallel to the case because the distance between the magnetic sensor and external case surface is changed by the moving. Further, in the case of moving the magnetic sensor along the circumference of the cylindrical external case, a complicated guide unit is required and the move of the magnetic sensor might result in noise generation in the detection signal. An object of the present invention is to detect a scratch on a cylindrical cell external case made of a magnetic material such as a steel sheet without such disadvantages.

Means for Solving the Problems

In the present invention, a scratch on a cylindrical cell external case is accurately inspected by a simple device in view of above object. Thus, the inspecting device of the invention is for inspecting a scratch on a cylindrical cell external case, and is characterized by comprising a rotation device for rotating the cell external case around the center axis of the cylindrical structure, magnetic poles facing each other for applying a magnetic flux to the cell external case, placed lateral to the cell external case, a magnetic sensor placed in the vicinity of the cell external case, a signal processing device for processing a signal detected by the magnetic sensor, and a display device for displaying a processing result.

As recited in claim 2, the magnetic sensor may be movable parallel to the center axis of the cylindrical cell external case in the axial direction, thereby scanning the cell external case in the axial direction to detect a scratch.

Further, as recited in claim 3, the inspecting device may have a plurality of magnetic sensors placed along the cylindrical cell external case, to detect a scratch.

The invention includes a method. Thus, as recited in claim 4, the inspecting method of the invention is for inspecting a scratch en a cylindrical cell external case, and is characterized by comprising using a unit for rotating the cell external case around the center axis of the cylindrical structure, a unit for applying a magnetic flux to the cell external case from magnetic poles facing each other placed lateral to the cell external case, and a unit for detecting a leak magnetic flux by a magnetic sensor placed in the vicinity of the cell external case, thereby comprising the steps of applying the magnetic flux to the cell external case while rotating the case, detecting the leak magnetic flux, and processing and displaying the detection signal.

Figure 1:
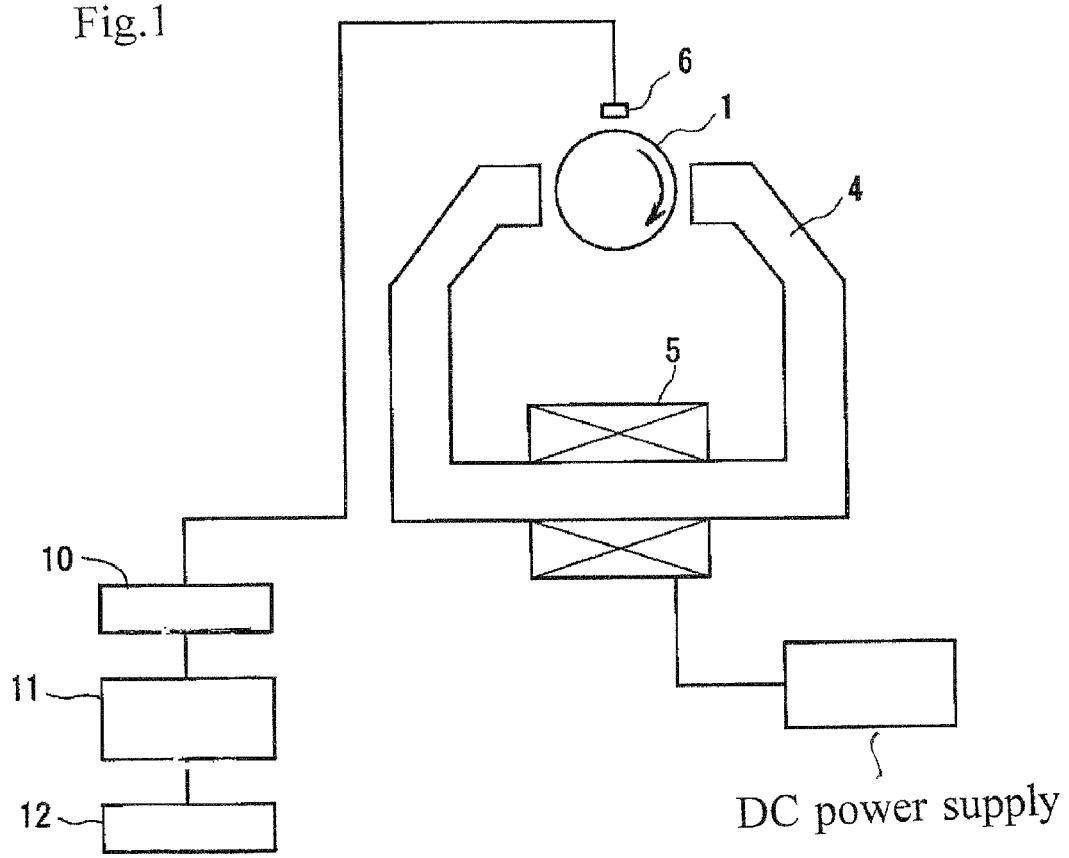
FIG. 1 is a schematic view showing a device for inspecting a cell external case according to the present invention.

In the drawings, reference numerals 1, 2, 4, 5, 6, 11, 12 represent a cell external case, a rotation device, a frame, an exciting coil, a magnetic sensor, a signal processing device, a display device, respectively.

BEST MODE FOR CARRYING OUT THE INVENTION

Figure 2:
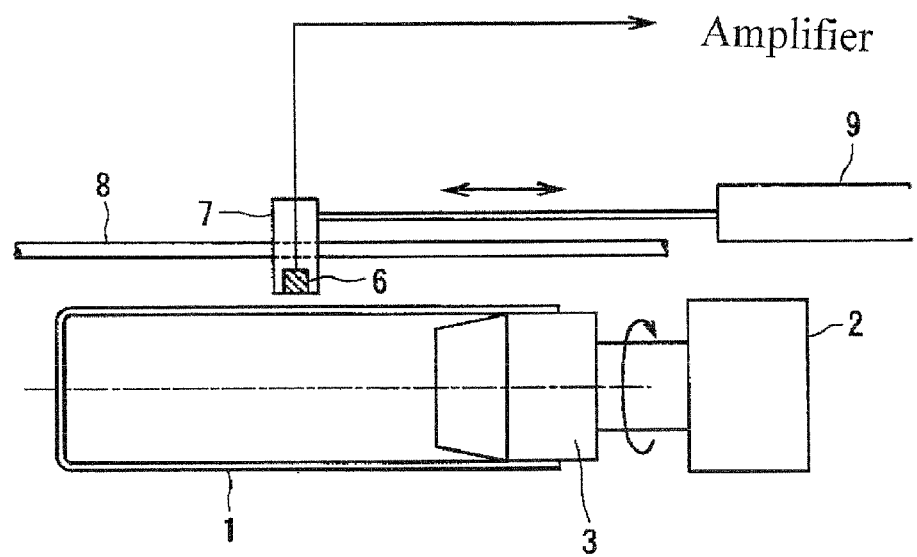
FIG. 2 is a view showing an arrangement of a magnetic sensor in the inspecting device of the invention.
Figure 3:
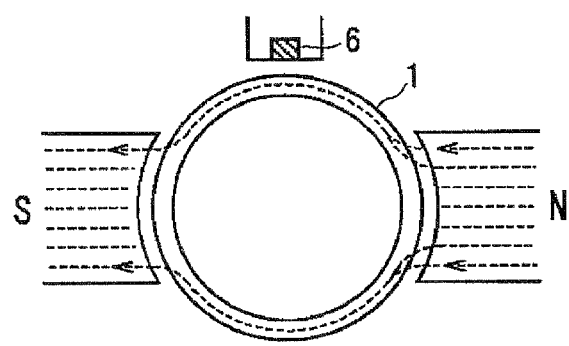
FIG. 3 is an explanatory view showing a magnetic flux flow in the cell external case.
Figure 4:
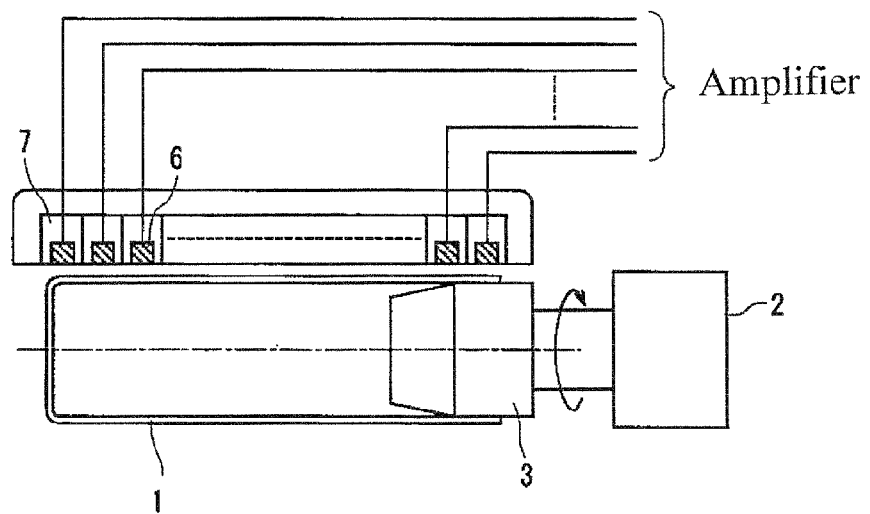
FIG. 4 is a view showing a modified arrangement of magnetic sensors in the invention.
Figure 7:
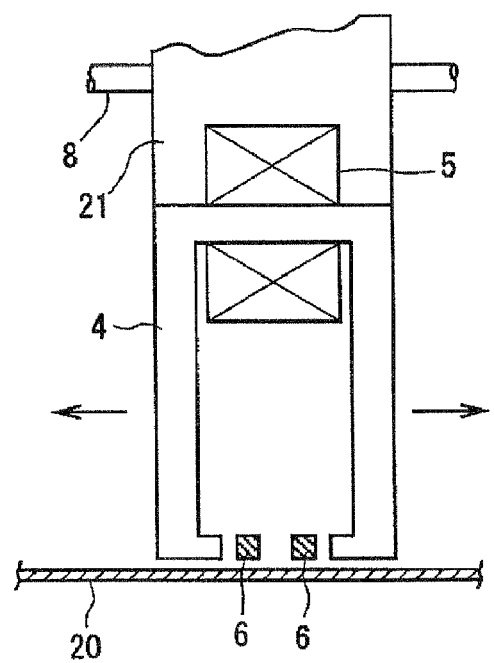
FIG. 7 is a view showing a conventional device for inspecting a scratch on a steel sheet by detecting a leak magnetic flux.

The device according to the present invention for inspecting a scratch on a cell external case will be described below with reference to the drawings. The cell external cases include cylindrical Cases prepared by deep drawing methods, drawing and ironing methods (DI methods), draw thin redraw methods (DTR methods), and methods of drawing followed by both of stretching and ironing. FIG. 1 is a schematic view showing the inspecting device according to the invention, and members in FIG. 1 corresponding to the members in the conventional device of FIG. 7 are represented by the same numerals. FIG. 2 is a view showing a structure of the cell external case and the magnetic sensor in the invention, and FIG. 3 is an explanatory view showing a flow of a magnetic flux in the cell external case. Further, FIG. 4 is a view showing a modified structure of magnetic sensors.

In FIGS. 1 and 2, the object material of the cell external case 1 is attached to a shaft 3 of a rotation device 2 such as a motor, to be rotatable around the center axis of the cylindrical structure. The shaft 3 is composed of a non-magnetic material to prevent a magnetic flux from passing therethrough. Though in this example the cell external case 1 is attached directly to the shaft 3 of the rotation device 2 such as a motor, the cell external case 1 may be rotated by a transmission system including a belt or a friction wheel etc. Both ends of a frame 4 are used as magnetic poles, and are arranged in the vicinity of the cell external case 1 in the radial direction, and an exciting coil 5 is attached to the center of the frame 4. In this example, the inspecting device is such a vertically arranged type device that the both ends of the frame 4 is located above and the exciting coil 5 is located below, and the rotation device 2 and the frame 4 are fixed to a frame not shown. Further, though the electromagnet is used in this example, a permanent magnet may be used instead of the electromagnet without the exciting coil 5.

A magnetic sensor 6 is located in the vicinity of the cell external case 1, e.g. at a distance of 1 mm. The magnetic sensor 6 is known one using a hall element, etc., and is attached to a detection head 7. The detection head 7 is fitted on a guide bar 8 fixed to a frame, and is slid in the axial direction of the cell external case 1 by an actuator 9. The detection head 7 may be moved by using a feed screw system instead of the actuator 9. A signal detected by the magnetic sensor 6 is input via an amplifier 10 into a signal processing device 11, processed to extract a scratch signal in the signal processing device 11, and transferred to a display device 12.

Then operation of the inspecting device and the inspecting method are described. When a current is applied from a DC power source to the exciting coil 5, the frame 4 is converted to an electromagnet, and an N pole and an S pole are generated at the ends of the frame 4 facing each other, placed in the vicinity of the rotating cell external case 1. Thus, as shown in FIG. 3, a magnetic flux flows from the N pole to the S pole through the cell external case 1. In the case of using a permanent magnet, its N pole and S pole are arranged such that the poles face each other with the cell external case 1 therebetween. It should be noted that, though the cell external case 1 is shown as a thicker one in FIG. 3 to facilitate understanding, the cell external case 1 actually has a small thickness of 0.1 to 0.2 mm.

The magnetic flux passes through the cell external case 1 mainly in the vicinity of the case surface, and when the case has a defect such as a scratch, the magnetic flux leaks from the surface of the cell external case 1. The presence of a scratch can be inspected by detecting the leak magnetic flux using the magnetic sensor 6. The cell external case 1 is rotated by the rotation device 2, whereby scratches can be detected over the entire circumference of the cylindrical cell external case 1 at the position of the magnetic sensor 6. In this process, though the entire circumference can be inspected only by one revolution of the external case 1 theoretically, it is preferred that the circumference be inspected by a plurality of revolutions from the viewpoint of increasing the inspection accuracy. Then, the magnetic sensor 6 is moved in the axial direction of the cell external case 1 to detect a scratch, so that the entire surface of the cell external case 1 can be inspected.

Instead of moving one magnetic sensor 6 in the axial direction, a plurality of magnetic sensors 6, which detect a scratch at each position at the same time, may be arranged along the cell external case 1 as shown in the modified arrangement of FIG. 4. In this case, the entire surface can be inspected without moving the magnetic sensor 6 in the width direction to repeat the detection, so that the inspection time can be greatly reduced, whereby the device is suitable for inspecting mass-produced cell external cases in the production line. Further, the magnetic sensors 6 are fixed, whereby noise due to move of the magnetic sensors is not generated. Also in this case, it is preferred that a plurality of revolutions of the cell external case be made to increase the inspection accuracy. In this modified arrangement example, the detection signals are transferred from the magnetic sensors 6 to the signal processing device 11 as a multichannel signal.

Figure 5:
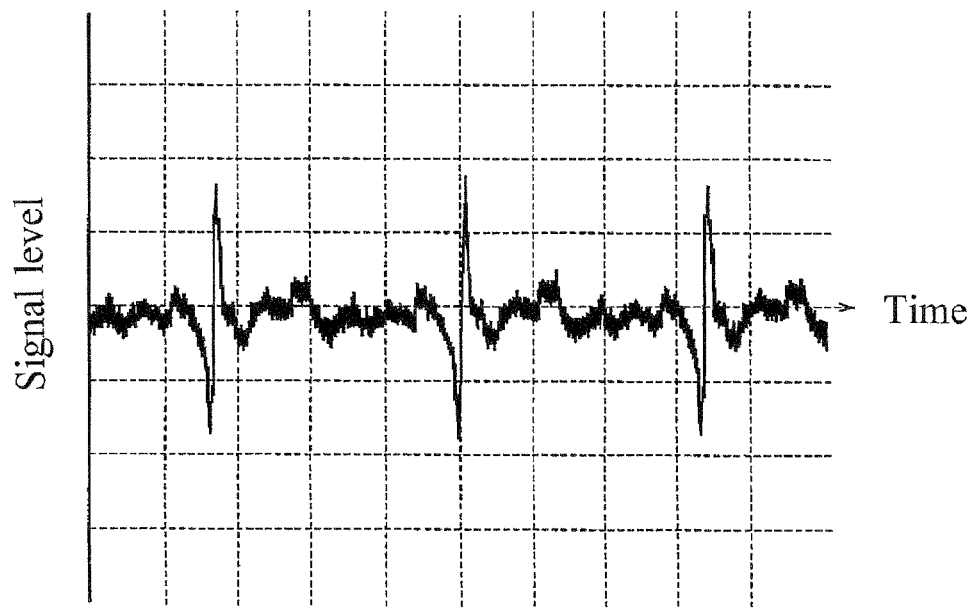
FIG. 5 is a diagram showing a result of an inspection according to the invention.
Figure 6:
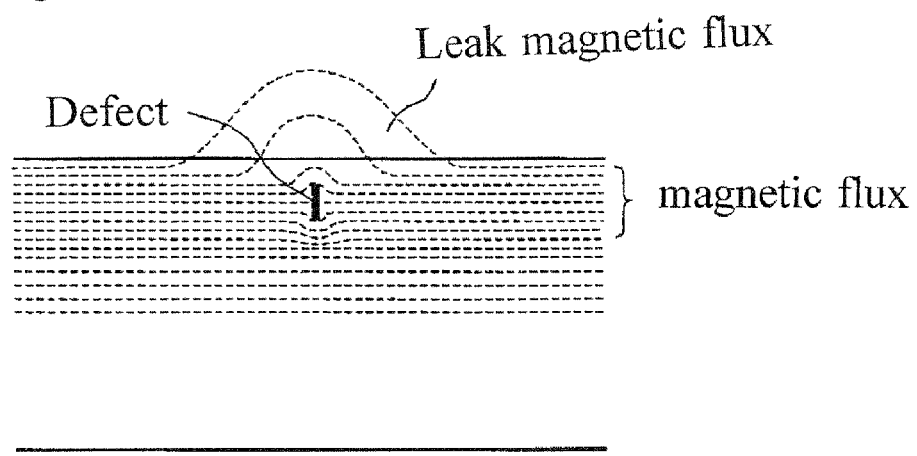
FIG. 6 is an explanatory view showing a leak magnetic flux.

A result of inspecting a scratch on a cell external case by the inspecting device of the invention is shown in FIG. 5. This is such that a fine scratch is made on the cell external case, a signal is detected by a magnetic sensor while rotating the cell external case, and the signal is transferred to a signal processing device and then shown in an oscilloscope of a display device. The transverse axis indicates the time, and the ordinate axis indicates the signal level. In the inspection result, sharp peaks in the signal level due to the surface scratch are shown for every revolution of the cell external case, and thus it is clear that the fine scratch can be detected by the device of the invention.

As described in detail above, in the invention, to inspect a scratch on a cylindrical cell external case made of a magnetic material such as a steel sheet, a magnetic flux is applied to the cell external case while rotating the case, a leak magnetic flux is detected by a magnetic sensor placed in the vicinity of the cell external case, and the obtained signal is shown in a display device. The inspecting device of the above example is such a vertically arranged type device that the both ends of the frame, used as magnetic poles, are located above, though it may be a horizontally arranged type device. Further, not only the oscilloscope but also various units can be used as the display device obviously, and for example the detection signal may be stored as digital data on a recording medium and then displayed.

INDUSTRIAL APPLICABILITY

In the present invention, the cell external case is rotated around the center axis of its cylindrical structure, a magnetic flux is applied to the revolving cell external case by a magnet, and a leak magnetic flux is detected by the magnetic sensor placed in the vicinity of the cell external case. The leak magnetic flux is generated when the cell external case has a scratch. Since the cylindrical cell external case is rotated around the center axis, the distance between the external case surface and the magnetic sensor is not changed, so that a scratch on the cell external case can be stably detected. Further, the inspecting device has the signal processing device and the display device for processing and displaying a detection signal from the magnetic sensor, so that the position of scratch can be accurately determined. Also the method of the invention according to claim 4 has the advantageous effects.

The magnetic sensor may be moved in the axial direction of the cylindrical cell external case as recited in claim 2, thereby scanning the cell external case surface in the axial direction. In this case, scratches in different positions can be detected only by one magnetic sensor.

A plurality of magnetic sensors may be placed along the cylindrical cell external case to detect a scratch as recited in claim 3, and in this case, the detection can be across the full width of the cell external case at the same time. Thus, the scratch inspection can be carried out over the entire surface only by one revolution of the cell external case essentially, whereby the inspecting time can be greatly reduced. Further, the magnetic sensors are not moved in the radial direction and axial direction of the cell external case, whereby noise due to move of the magnetic sensors is not generated in the detection signal.

The invention claimed is:

1. An inspecting device for inspecting a scratch on a cylindrical cell external case, comprising:
   a rotation device for rotating the cell external case around the center axis of a cylindrical structure,
   magnetic poles facing each other for applying a magnetic flux to the cell external case, placed lateral to the case,
   a magnetic sensor placed in the vicinity of the cell external case,
   a detection head, the magnetic sensor attached to the detection head, and the detection head connected to an actuator so as to be slid in the axial direction of the cell external case by the actuator,
   a signal processing device for processing a signal detected by the magnetic sensor, and
   a display device for displaying a processing result,
   wherein the inspecting device comprises a plurality of magnetic sensors placed along the cylindrical cell external case.

2. The inspecting device according to claim 1, wherein the magnetic sensors are movable parallel to the center axis of the cylindrical cell external case in an axial direction.

3. The inspecting device according to claim 1, wherein a length of the plurality of magnetic sensors is equal to or larger than a length of the cylindrical cell external case in the axial direction.

* * * * *